United States Patent [19]

Goldman et al.

[11] Patent Number: 5,436,342
[45] Date of Patent: Jul. 25, 1995

[54] CONDENSED QUINOLYL-DIHYDROPYRIDINES, PROCESSES FOR THEIR PREPARATION AND THEIR USE IN MEDICAMENTS

[75] Inventors: Siegfried Goldman, Wuppertal; Jürgen Stoltefuss, Haan; Alexander Straub, Wuppertal; Martin Bechem, Wuppertal; Rainer Gross, Wuppertal; Siegbert Hebisch, Wuppertal; Joachim Hütter, Wuppertal; Howard-Paul Rounding, Wuppertal, all of Germany

[73] Assignee: Bayer Aktiengesellschaft, Leverkusen, Germany

[21] Appl. No.: 231,010

[22] Filed: Apr. 20, 1994

[30] Foreign Application Priority Data

Apr. 27, 1993 [DE] Germany ............... 43 13 690.7

[51] Int. Cl.⁶ ............... C07D 495/04; C07D 401/04; C07D 403/11; A61K 31/495
[52] U.S. Cl. .................. 546/167; 544/363
[58] Field of Search ............ 546/167; 514/314; 544/363

[56] References Cited

U.S. PATENT DOCUMENTS

| | | | |
|---|---|---|---|
| 4,145,432 | 3/1979 | Sato | 429/266 |
| 4,248,873 | 2/1981 | Bossert et al. | 424/256 |
| 5,100,900 | 3/1992 | Stoltefuss et al. | 514/314 |
| 5,204,472 | 4/1993 | Stoltefuss et al. | 546/168 |

FOREIGN PATENT DOCUMENTS 157324  3/1989  European Pat. Off. .
452712  3/1991  European Pat. Off. .

*Primary Examiner*—David B. Springer
*Attorney, Agent, or Firm*—Sprung Horn Kramer & Woods

[57] ABSTRACT

The invention relates to novel, condensed 4-quinolyl-dhydropyridines of the general formula (I)

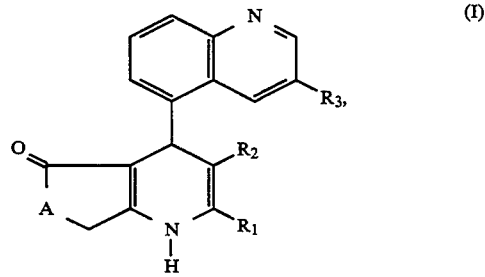

in which A, $R_1$, $R_2$ and $R_3$ have the meaning given in the description, to processes for their preparation and to their use in medicaments, in particular in agents for treating angiocardiopathies.

9 Claims, No Drawings

CONDENSED QUINOLYL-DIHYDROPYRIDINES, PROCESSES FOR THEIR PREPARATION AND THEIR USE IN MEDICAMENTS

The invention relates to novel condensed 4-quinolyl-dihydropyridines, processes for their preparation and their use in medicaments, in particular in agents for treating angiocardiopathies.

It is already known that 1,4-dihydropyridines possess vasodilatory properties and can be used as coronary agents and antihypertensive agents. In addition, it is known that 1,4-dihydropyridines bring about an inhibition of the contractile power of smooth and cardiac muscles and can be employed for treating coronary and vascular diseases. The positive inotropic effect of some 4-quinolyl-dihydropyridines is also already known (U.S. Pat. No. 5,100,900).

It could not have been foreseen from a knowledge of the state of the art that the compounds according to the invention would have the effect of amplifying the contractile power of cardiac muscle in a positively inotropic manner, while at the same time having little or no vascular effect.

The present invention relates to condensed 4-quinolyl-dihydropyridines of the general formula (I)

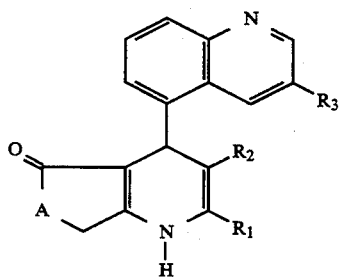

in which

A represents a sulphur atom or the —CH$_2$-group,

R$^1$ represents hydrogen, amino, cyano, formyl or trifluoromethyl, or represents straight-chain or branched alkyl having up to 8 carbon atoms, which is optionally substituted by hydroxyl or by a group of the formula —NR$^6$R$^7$, —O—CO—R$^8$, —O—(CH$_2$)$_a$—OR$^{8'}$ or —O—(CH$_2$)$_b$—NR$^9$R$^{10}$, in which R$^6$, R$^7$, R$^9$ and R$^{10}$ are identical or different and denote hydrogen, phenyl or straight-chain or branched alkyl having up to 6 carbon atoms, R$^8$ and R$^{8'}$ are identical or different and denote straight-chain or branched alkyl having up to 6 carbon atoms, and a and b are identical or different and denote a number 2, 3, 4 or 5, R$^2$ represents a group of the formula —CO—NR$^{11}$R$^{12}$ or —CO—D—R$^{13}$, in which R$^{11}$ and R$^{12}$ are identical or different and denote hydrogen, a straight-chain, branched, cyclic, saturated or unsaturated hydrocarbon radical having up to 8 carbon atoms, which is optionally substituted by halogen, hydroxyl or cyano, or by aryl, aryloxy or arylthio having in each case 6 to 10 carbon atoms, or by a 5- to 7-membered, saturated or unsaturated heterocycle having up to 3 heteroatoms selected from the group comprising S, N or O, where the cycles, for their part, can be substituted by halogen or cyano, or by straight-chain or branched alkyl, alkoxy, alkylthio, alkoxycarbonyl, halogenoalkyl, halogenoalkoxy or halogenoalkylthio having in each case up to 4 carbon atoms, or aryl having 6 to 10 carbon atoms or a 5- to 7-membered, saturated or unsaturated heterocycle having up to 3 heteroatoms selected from the group comprising S, N or O, which are optionally substituted identically or differently up to 2 times by halogen or cyano, or by straight-chain or branched alkyl, alkoxy, alkylthio, alkoxycarbonyl, halogenoalkyl, halogenoalkoxyor halogenoalkylthio having in each case up to 4 carbon atoms, or R$^{11}$ and R$^{12}$, together and with the inclusion of the nitrogen atom, form a 3- to 8-membered, saturated or unsaturated heterocycle, which is optionally interrupted by an oxygen atom or by a radical of the formula S(O)$_d$, —CO— or —NR$^{15}$, in which d denotes a number 0, 1 or 2, R$^{15}$ denotes hydrogen or aryl having 6 to 10 carbon atoms, which is optionally substituted identically or differently up to 2 times by halogen or cyano, or by straight-chain or branched alkyl, alkoxy, alkylthio or alkoxycarbonyl having in each case up to 8 carbon atoms, or by halogenoalkyl, halogenoalkoxy or halogenoalkylthio having in each case up to 4 carbon atoms, or denotes a cyclic, saturated or unsaturated, straight-chain or branched hydrocarbon radical having up to 8 carbon atoms, which is optionally substituted by hydroxyl or halogen, or by aryl having 6 to 10 carbon atoms, or by a 5- to 7-membered, saturated or unsaturated heterocycle having up to 3 heteroatoms selected from the group comprising S, N or O, where the cycles, for their part, can be substituted identically or differently up to 2 times by halogen or cyano, or by straight-chain or branched alkyl, alkoxy, alkylthio, alkoxycarbonyl, halogenoalkyl, halogenoalkoxy or halogenoalkylthio having in each case up to 4 carbon atoms, and the heterocycle is optionally substituted by straight-chain or branched alkoxy or alkylthio having in each case up to 4 carbon atoms, by halogen, by aryl having 6 to 10 carbon atoms, by a 5- to 7-membered, saturated or unsaturated heterocycle having up to 3 heteroatoms selected from the group comprising S, N or O, or by straight-chain or branched alkyl having up to 4 carbon atoms which, for its part, can be substituted by aryl having 6 to 10 carbon atoms, D denotes a direct linkage or an oxygen atom, R$^{13}$ denotes hydrogen or aryl having 6 to 10 carbon atoms or a 5- to 7-membered, saturated or unsaturated heterocycle having up to 3 heteroatoms selected from the group comprising S, N or O, where the cycles are optionally substituted identically or differently up to 3 times by halogen or cyano, or by straight-chain or branched alkyl, alkoxy, alkylthio, alkoxycarbonyl, halogenoalkyl, halogenoalkoxy or halogenoalkylthio having in each case up to 4 carbon atoms, or denotes a cyclic, straight-chain or branched, saturated or unsaturated hydrocarbon radical having up to 10 carbon atoms, which is optionally interrupted identically or differently up to 3 times by oxygen or by —CO—, —CO—NH—, —O—CO—, —CO—O—, —NH—CO—, —SO$_2$—NH—, —NH—SO$_2$—, —S(O)$_a$— or —NR$^{16}$, in which
- e has the abovementioned meaning of d and is identical to or different from the latter,
- $R^{16}$ has the abovementioned meaning of $R^{15}$ and is identical to or different from the latter, or the carbon radical is optionally interrupted identically or differently up to 3 times by arylidene having 6 to 10 carbon atoms or by heterocyclic residues of the formulae

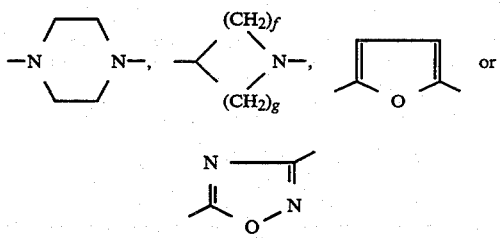

in which
- f and g are identical or different and denote a number 1 or 2, and where the aryl and hetero cycles, for their part, can be substituted by halogen or cyano, or by straight-chain or branched alkyl, alkoxy, alkylthio, alkoxycarbonyl, halogenoalkyl, halogenoalkoxy or halogenoalkylthio having in each case up to 4 carbon atoms,
and the hydrocarbon radical is optionally substituted identically or differently up to 3 times by cycloalkyl having 3 to 8 carbon atoms, by halogen, nitro, cyano, hydroxyl or —O—$NO_2$, or by straight-chain or branched alkylthio, alkoxy or acyloxy having in each case up to 8 carbon atoms, or by aryl, aryloxy or arylthio having in each case 6 to 10 carbon atoms, or by a 5- to 7-membered, saturated or unsaturated heterocycle having up to 3 heteroatoms selected from the group comprising S, N or O, where the cycles, for their part, can be substituted identically or differently up to 3 times by halogen or cyano, or by straight-chain or branched alkyl, alkoxy, alkylthio, alkoxycarbonyl, halogenoalkyl, halogenoalkoxy or halogenoalkylthio having in each case up to 4 carbon atoms, or the hydrocarbon radical can be substituted by a group of the formula —$CO_2$—$R^{17}$, —$CONR^{18}R^{19}$ or —$NR^{20}R^{21}$,
in which
- $R^{17}$ has the abovementioned meaning of $R^{15}$ and is identical to or different from the latter
and
- $R^{18}$, $R^{19}$, $R^{20}$ and $R^{21}$ have the abovementioned meaning of $R^{11}$ and $R^{12}$ and are identical to or different from these latter, and
- $R^3$ represents aryl having 6 to 10 carbon atoms, which is optionally substituted identically or differently up to 2 times by halogen, nitro, cyano, trifluoromethyl, trifluoromethoxy or trifluoromethylthio, or by straight-chain or branched alkyl, alkoxy or alkoxycarbonyl having in each case up to 8 carbon atoms, or by carboxyl, or represents thienyl or pyridyl which are optionally substituted by halogen and salts thereof.

Physiologically harmless salts can be salts of the compounds according to the invention with inorganic or organic acids. Those salts which are preferred are salts with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid or benzoic acid, or methanesulphonic acid, ethanesulphonic acid, phenylsulphonic acid, toluenesulphonic acid, or naphthalenedisulphonic acid.

The compounds according to the invention exist in stereoisomeric forms which either do (enantiomers) or do not (diastereomers) relate to each other as image and mirror image. The invention relates both to the antipodes and the racemic forms as well as to the diastereomeric mixtures. Both the racemic forms and the diastereomers can be separated, in a known manner, into the stereoisomerically uniform constituents (cf. E. L. Eliel, Stereochemistry of Carbon Compounds, McGraw Hill, 1962).

Compounds of the general formula (I) are preferred, in which
- A represents a sulphur atom or the —$CH_2$-group,
- $R^1$ represents hydrogen, amino, cyano, formyl or trifluoromethyl, or represents straight-chain or branched alkyl having up to 6 carbon atoms, which is optionally substituted by hydroxyl or by a group of the formula —$NR^6R^7$, —O—CO—$R^8$, —O—($CH_2$)$_a$—$OR^{8'}$ or —O—($CH_2$)$_b$, —$NR^9R^{10}$,
in which
- $R^6$, $R^7$, $R^9$ and $R^{10}$ are identical or different and denote hydrogen or straight-chain or branched alkyl having up to 4 carbon atoms,
- $R^8$ and $R^{8'}$ are identical or different and denote straight-chain or branched alkyl having up to 4 carbon atoms,
and
- a and b are identical or different and denote a number 2, 3 or 4,
- $R^2$ represents a group of the formula —CO—$NR^{11}R^{12}$ or —CO—D—$R^{13}$,
in which
- $R^{11}$ and $R^{12}$ are identical or different and denote hydrogen, a straight-chain, branched, cyclic, saturated or unsaturated hydrocarbon radical having up to 6 carbon atoms, which is optionally substituted by fluorine, chlorine, hydroxyl or cyano, or by phenyl, phenyloxy, phenylthio or pyridyl, where the cycles, for their part, can be substituted by fluorine or chlorine, or by alkyl, alkoxy or alkoxycarbonyl having in each case up to 2 carbon atoms, or by trifluoromethyl or trifluoromethoxy, or denote phenyl or pyridyl, which are optionally substituted by fluorine or chlorine, or by straight-chain or branched alkyl, alkoxy, alkylthio or alkoxycarbonyl having in each case up to 4 carbon atoms, or by trifluoromethyl or trifluoromethoxy,
or
- $R^{11}$ and $R^{12}$, together and with the inclusion of the nitrogen atom, form a 5- to 7-membered, saturated or unsaturated heterocycle, which is optionally interrupted by an oxygen atom or by a radical of the formula S(O)$_d$, —CO— or —$NR^{15}$,
in which
- d denotes a number 0, 1 or 2,
- $R^{15}$ denotes hydrogen or phenyl, which is optionally substituted by fluorine or chlorine, or by straight-chain or branched alkyl or alkoxy having in each case up to 4 carbon atoms, or by trifluoromethyl or trifluoromethoxy, or denotes a cyclic, saturated or unsaturated, straight-chain or branched hydrocarbon radical having up to 4 carbon atoms, which is optionally substituted by fluorine or chlorine, or by phenyl or a 5- to 7-membered, saturated or unsaturated heterocycle having up to 2 heteroatoms selected from the group comprising O, S and N, which, for their part, can be substituted by fluorine or chlorine, or by straight-chain or branched alkyl or alkoxy having in each case up to 4 carbon atoms, or by trifluoromethyl or trifluoromethoxy, D denotes a direct linkage or an oxygen atom, $R^{13}$ denotes hydrogen or phenyl or pyridyl, which are optionally substituted by fluorine or chlorine, or by straight-chain or branched alkyl, alkoxy, alkylthio or alkoxycarbonyl having in each case up to 4 carbon atoms, or by trifluoromethyl or trifluoromethoxy, or denotes a cyclic, straight-chain or branched, saturated or unsaturated hydrocarbon radical having up to 8 carbon atoms, which is optionally interrupted identically or differently up to 2 times by oxygen or by —CO—, —CO—NH—, —O—CO—, —CO—O—, —NH—CO—, —SO$_2$—NH—, —NH—SO$_2$—, —S(O)$_e$— or —NR$^{16}$, in which e has the abovementioned meaning of d and is identical to or different from the latter, $R^{16}$ has the abovementioned meaning of $R^{15}$ and is identical to or different from the latter, or the hydrocarbon radical is optionally interrupted by phenylidene or by heterocyclic residues of the formulae

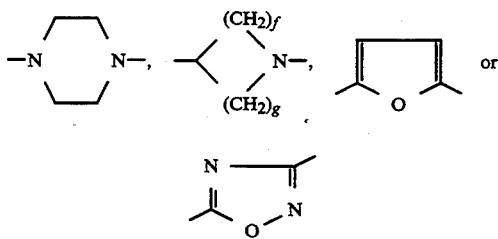

in which, f and g are identical or different and denote a number 1 or 2, and the hydrocarbon radical is optionally substituted identically or differently up to 2 times by cyclopropyl, cyclobutyl, cyclopentyl, cyclohexyl, fluorine, chlorine, nitro, cyano, hydroxyl or —O—NO$_2$, or by straight-chain or branched alkylthio, alkoxy or acyloxy having in each case up to 4 carbon atoms, or by phenyl, phenoxy, phenylthio or pyridyl, which, for their part, can be substituted identically or differently up to 2 times by fluorine, chlorine or cyano, or by straight-chain or branched alkyl, alkoxy, alkylthio or alkoxycarbonyl having in each case up to 4 carbon atoms, or by trifluoromethyl or trifluoromethoxy, or the hydrocarbon radical can be substituted by a group of the formula CO$_2$—R$^{17}$, —CONR$^{18}$R$^{19}$ or —NR$^{20}$R$^{21}$, in which $R^{17}$ has the abovementioned meaning of $R^{15}$ and is identical to or different from the latter and $R^{18}$, $R^{19}$, $R^{20}$ and $R^{21}$ have the abovementioned meaning of $R^{11}$ and $R^{12}$ and are identical to or different from these latter, and $R^3$ represents phenyl, which is optionally substituted by fluorine, chlorine, nitro, cyano or trifluoromethyl, or by straight-chain or branched alkyl or alkoxy having in each case up to 6 carbon atoms, or by hydroxyl, or represents thienyl or pyridyl, which are optionally substituted by fluorine, chlorine or bromine, and salts thereof.

Compounds of the general formula (I) are particularly preferred in which

A represents a sulphur atom or the —CH$_2$-group, $R^1$ represents hydrogen, amino, cyano, formyl or trifluoromethyl, or represents straight-chain or branched alkyl having up to 3 carbon atoms, which is optionally substituted by hydroxyl or by a group of the formula —NR$^6$R$^7$, —O—CO—R$^8$, —O—(CH$_2$)$_a$—OR$^{8'}$ or —O—(CH$_2$)$_b$, —NR$^9$R$^{10}$, in which $R^6$, $R^7$, $R^9$ and $R^{10}$ are identical or different and denote hydrogen, methyl or ethyl, $R^8$ and $R^{8'}$ are identical or different and denote methyl or ethyl, and a and b are identical or different and denote a number 2 or 3, $R^2$ represents a group of the formula —CO—NR$^{11}$R$^{12}$ or —CO—D—R$^{13}$, in which $R^{11}$ and $R^{12}$ are identical or different and denote hydrogen, a straight-chain, branched, cyclic, saturated or unsaturated hydrocarbon radical having up to 6 carbon atoms, which is optionally substituted by fluorine, chlorine, phenyl or pyridyl, or denote phenyl or pyridyl, which are optionally substituted by fluorine, chlorine, methyl or methoxy, or $R^{11}$ and $R^{12}$, together and with the inclusion of the nitrogen atom, form a 5- to 6-membered, unsaturated heterocycle, which is optionally interrupted by oxygen or sulphur or the radical NR$^{15}$, in which $R^{15}$ denotes hydrogen or phenyl, which is optionally substituted by fluorine, chlorine, methyl, methoxy or trifluoromethyl, or denotes a cyclic, saturated or unsaturated, straight-chain or branched hydrocarbon radical having up to 4 carbon atoms, which is optionally substituted by phenyl or pyridyl, D denotes a direct linkage or an oxygen atom, $R^{13}$ denotes hydrogen or phenyl, which is optionally substituted by fluorine, chlorine, methyl, methoxy or trifluoromethyl, or denotes a cyclic, straight chain or branched saturated or unsaturated hydrocarbon radical having up to 6 carbon atoms, which is optionally interrupted by oxygen or sulphur or by —CO—, —CO—NH—, —O—CO—, —CO—O—, —NH—CO—, —SO$_2$—NH—, —NH—SO$_2$— or —NR$^{16}$, in which $R^{16}$ has the abovementioned meaning of $R^{15}$ and is identical to or different from the latter, or the hydrocarbon radical is optionally interrupted by phenylidene or by heterocyclic residues of the formulae

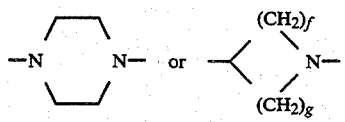 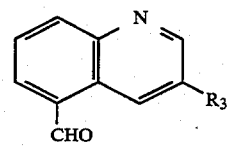

in which,
  f and g are identical or different and denote a number 1 or 2,
and the hydrocarbon radical is optionally substituted by cyclopropyl, cyclobutyl, cyclopentyl, cyclohexyl, fluorine, chlorine, nitro or hydroxyl, or by straight-chain or branched alkyl thio or alkoxy having in each case up to 5 carbon atoms, or by phenyl, phenoxy, phenylthio or pyridyl, which, for their part, can be substituted by fluorine, chlorine, methyl, methoxy or methylthio, or can be substituted by a group of the formula —CO$_2$—R$^{17}$, —CONR$^{18}$R$^{19}$ or —NR$^{20}$R$_{21}$,
in which
  R$^{17}$ has the abovementioned meaning of R$^{15}$ and is identical to or different from the latter
and
  R$^{18}$, R$^{19}$, R$^{20}$ and R$^{21}$ have the abovementioned meaning of R$^{11}$ and R$^{12}$ and are identical to or different from these latter,
and
  R$^3$ represents phenyl, which is optionally substituted by fluorine, chlorine, nitro or trifluoromethyl, or by straight-chain or branched alkyl or alkoxy having in each case up to 4 carbon atoms, or represents thienyl, which is optionally substituted by fluorine or chlorine, and salts thereof.

Compounds of the general formula (I) are very particularly preferred
in which
  A represents a sulphur atom or the —CH$_2$— group,
  R$^1$ represents hydrogen, amino or methyl,
  R$^2$ represents a group of the formula —CO—NR$^{11}$R$^{12}$ or —CO—D—R$^{13}$,
in which
  R$^{11}$ and R$^{12}$ are identical or different and denote hydrogen or a straight-chain, branched or cyclic alkyl radical having up to 6 carbon atoms,
  D denotes an oxygen atom,
  R$^{13}$ denotes hydrogen or straight-chain or branched alkyl having up to 6 carbon atoms, which is optionally substituted by cyclopropyl, cyclobutyl, cyclopentyl or cyclohexyl, or by straight-chain or branched alkoxy or alkylthio having in each case up to 4 carbon atoms, or by fluorine, phenyl, phenoxy or NR$^{20}$R$^{21}$,
in which
  R$^{20}$ and R$^{21}$ in each case represent hydrogen, or alkyl having up to 4 carbon atoms, which is optionally substituted by phenyl, or phenyl, and
  R$^3$ represents phenyl, which is optionally substituted by fluorine, chlorine, methyl or methoxy, and salts thereof.

In addition, a process for preparing the compounds of the general formula (I) according to the invention has been found, characterized in that
in the case where A represents the —CH$_2$— group,
[A] Compounds of the general formula (II)

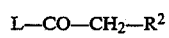

in which
  R$^3$ has the abovementioned meaning, are initially reacted with acyl compounds of the general formula (III)

$$L—CO—CH_2—R^2 \quad (III)$$

in which
  R$^2$ has the abovementioned meaning and
  L has the abovementioned meaning of R$^1$, where, in the case of the hydroxyl and/or amino functions, these functions are optionally present in protected form,
optionally with the isolation of the ylidene compounds of the general formula (IV)

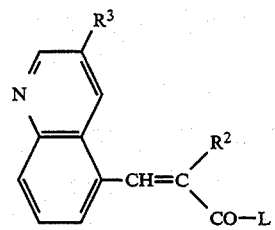

in which
  R$^2$, R$^3$ and L have the abovementioned meaning and subsequently reacted with the compound of the formula (V)

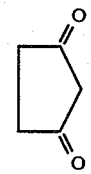

and a reactive ammonium compound, e.g. ammonium acetate, optionally with the isolation of the intermediates of the general formula (VI)

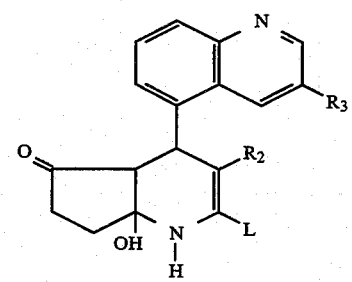

in which
  R$^2$, R$^3$ and L have the abovementioned meaning,
  in inert solvents,
and, in the case of the compounds of the general formula (VI), water is eliminated, in a last step, in the presence of an auxiliary agent, or

[B] compounds of the general formula (II) are reacted directly with the compound of the formula (V) and compounds of the general formula (VII)

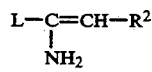

in which

L and $R^2$ have the abovementioned meaning, and

[C] in the case of the compounds of the general formula (I), in which A represents a sulphur atom, compounds of the general formula (II) are initially reacted with compounds of the general formula (III), optionally with the isolation of the corresponding ylidene compounds of the general formula (IV), as described under [A], and subsequently reacted either with compounds of the general formula (VIII)

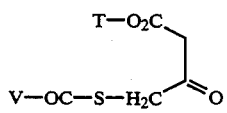

in which

T and V are identical or different and denote $C_1$-$C_6$-alkyl, in the presence of ammonia or ammonium salts, or directly with compounds of the general formula (IX)

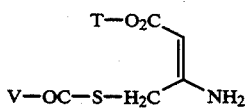

in which

T and V have the abovementioned meaning, optionally with the isolation of the compounds of the general formula (X)

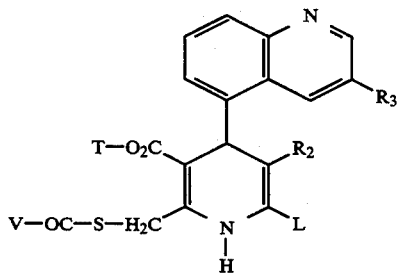

in which $R^2$, $R^3$, L, V and T have the abovementioned meaning, in inert solvents, and the compounds of the general formula (X) are then cyclized with bases or acids, or

[D] Compounds of the general formula (XI)

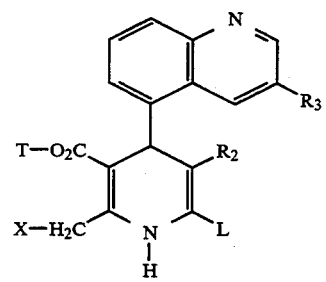

in which $R^2$, $R^3$, T and L have the abovementioned meaning, and

X represents halogen, are converted, by reaction in inert solvents with salts of thioacyl acids, into the compounds of the general formula (X) and cyclized as described under [B], or

[E] Compounds of the general formula (II) are initially reacted with compounds of the general formula (VIII), optionally with the isolation of the corresponding ylidene compound of the general formula (XII)

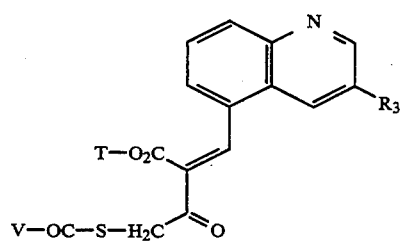

in which $R^3$, T and V have the abovementioned meaning, and, in a second step, a reaction with compounds of the general formula (XIII)

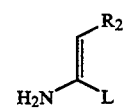

in which $R^2$ and L have the abovementioned meaning, is carried out in inert solvents.

The processes according to the invention can be illustrated, by way of example, by the following formula schemes:

[A]

-continued

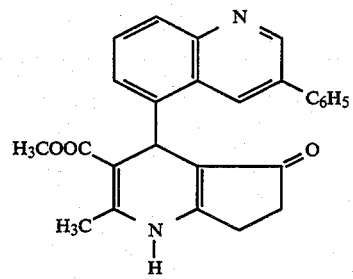

[B] 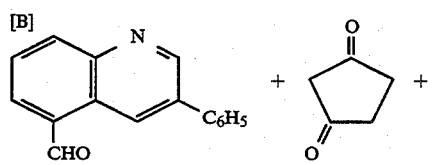 + 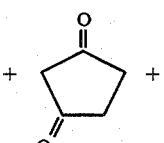 +

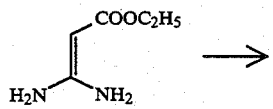

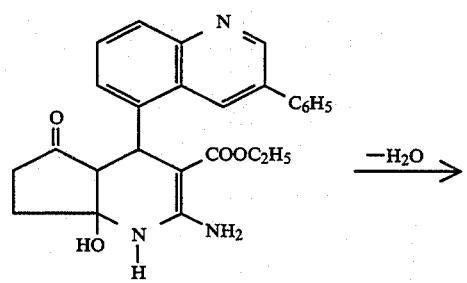 —H₂O →

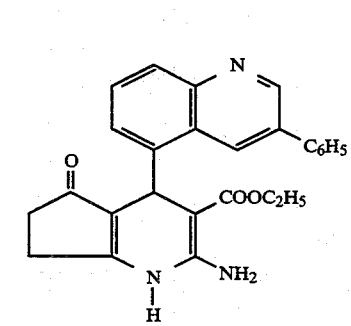

[D] 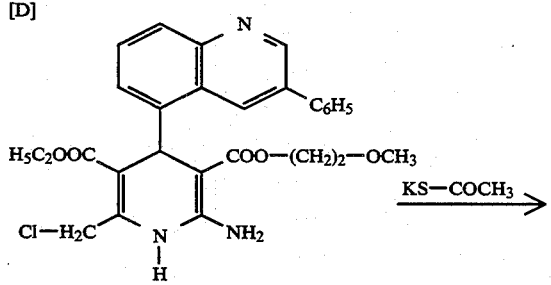 KS—COCH₃ →

-continued

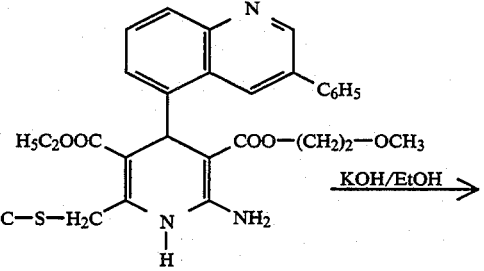 KOH/EtOH →

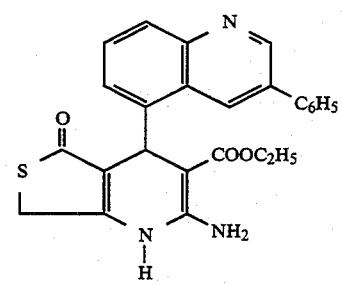

All inert organic solvents which are not altered under the reaction conditions are suitable for use as solvents in these processes. These solvents preferably include alcohols, such as methanol, ethanol, propanol or isopropanol, or ethers, such as diethyl ether, dioxane, tetrahydrofuran, glycol dimethyl ether, or diethylene glycol dimethyl ether, acetonitrile, or amides, such as hexamethylphosphoric triamide or dimethylformamide, or acetic acid, or halogenated hydrocarbons, such as methylene chloride or carbon tetrachloride, or hydrocarbons, such as benzene or toluene. It is likewise possible to use mixtures of the said solvents. Those which are preferred, depending on the particular process variant [A], [B], [C], [D] and [E], are methanol, isopropanol, ethanol and n-propanol, acetonitrile or tetrahydrofuran.

The reaction temperatures can be varied over a relatively wide range. In general, temperatures of between +10° C. and 150° C., preferably of between +20° C. and +100° C., are employed. Use of the boiling temperature of the relevant solvent is particularly favoured.

The reaction can be carried out under atmospheric pressure, but also under elevated or reduced pressure (e.g. 0.5 to 3 bar). In general, atmospheric pressure is employed.

All esters or enantiomerically pure alcohols, such as, for example, 2-butanol, 1-phenylethanol, lactic acid, lactic esters, mandelic acid, mandelic esters, 2-aminoalcohols, sugar derivatives, hydroxyamino acid derivatives, and many other enantiomerically pure alcohols as well, are suitable for use as chiral ester residues.

The diastereomers are in general separated either by fractional crystallization, by column chromatography or by Craig partition. The optimum method must be determined from case to case; it is sometimes also expedient to use combinations of the individual methods. Separation by crystallization or by Craig partition, or a combination of the two methods, is particularly suitable.

Some of the compounds of the general formula (II) are known and can be prepared in accordance with customary methods, by, for example, oxidizing the corresponding alkyl quinolines or hydroxyalkyl quinolines, or reducing the corresponding carboxy quinolines.

Alternatively, 4-amino-3-hydroxyphthalide, which is obtained by customary hydrogenation of 4-nitro-3-hydroxyphthalide, which is known from the literature, in the presence of a catalyst, preferably using palladium/barium sulphate, can also be reacted with compounds of the general formula $R^3$—$CH_2$—CHO, some of which are known, to give, via the corresponding carboxylic acids, compounds of the general formula (II).

The compounds of the general formulae (III), (IV), (V), (VI), (VII), (IX), (XII) and (XIII) are known or can be prepared in accordance with customary methods.

The compounds of the general formula (XI) are novel, but can be prepared in accordance with known methods by, for example, reacting benzylidene compounds of the general formula (IV) with chloroacetoacetic esters and ammonium compounds.

The compounds of the general formula (VIII) are novel, but can be prepared in accordance with the known methods. The compounds of the general formula (X) are novel and can then be prepared as described above.

The above preparation processes are given solely for clarification. The preparation of the compounds of the formula (I) is not restricted to these processes, but any modification of these processes is applicable in the same way for preparing the compounds according to the invention.

The compounds according to the invention exhibit a valuable spectrum of pharmacological activity which could not have been foreseen. They exert an influence on the contractile power of the heart and on the tone of smooth musculature. They can therefore be employed in medicaments as coronary therapeutic agents in order to influence pathologically altered blood pressure and for treatment of cardiac insufficiency. In addition to this, they can be used for treating disturbances of cardiac rhythm, for lowering blood sugar, for detumescing mucus membranes and for affecting salt and fluid balance.

The cardiac and vascular effects were discovered using the isolated perfused heart of the guinea pig. For this purpose, hearts are used which are taken from guinea pigs of from 250 to 350 g in weight. The animals are killed by a blow to the head, the thorax is opened and a metal canula is tied into the aorta which has been freed by dissection. The heart, together with the lungs, is separated out from the thorax and connected to the perfusion apparatus via an aorta canula while perfusing continuously. The lungs are detached at the lung roots. A Krebs-Henseleit solution (118.5 mmol/l NaCl, 4.75 mmol/l KCl, 1.19 mmol/l $KH_2PO_4$, 1.19 mmol/l $MgSO_4$, 25 mmol/l $NaHCO_3$, 0.013 mmol/l $Na_2EDTA$), whose $CaCl_2$ content is 1.2 mmol/l, is used as the perfusion medium. 10 mmol/l glucose is added as the energy-supplying substrate. Prior to the perfusion, the solution is filtered in order to render it free of particles. The solution is gassed with Carbogen (95% $O_2$, 5% $CO_2$) in order to maintain the pH at 7.4. The hearts are perfused at a constant flow (10 ml/min) and at 32° C. using a peristaltic pump.

In order to measure the cardiac function, a latex balloon, which is filled with liquid and which is connected to a pressure sensor via a liquid column, is introduced through the left auricle into the left ventricle and the isovolumetric contractions are registered on a high-speed recorder. The perfusion pressure is registered by means of a pressure sensor which is connected to the perfusion system in front of the heart. Under these conditions, a decline in the perfusion pressure indicates coronary dilatation while an increase or decrease in the amplitude of contraction of the left ventricle indicates a fall or rise, respectively, in cardiac contractility. The compounds according to the invention are perfused into the perfusion system in suitable dilutions a short distance in front of the isolated heart.

The novel active compounds can be converted in a known manner into the customary formulation, such as tablets, coated tablets, pills, granules, aerosols, syrups, emulsions, suspensions and solutions, using inert, non-toxic, pharmaceutically suitable, carrier substances or solvents. The therapeutically active compound should in each case be present at a concentration of from about 0.5 to 90% by weight of the total mixture, i.e. in quantities which are sufficient to achieve the dosing latitude indicated.

The formulations are prepared, for example, by extending the active compounds with solvents and/or carrier substances, optionally using emulsifying agents and/or dispersing agents, it being possible, for example in the case where water is used as the diluent, optionally to use organic solvents as auxiliary solvents.

Administration is effected in a customary manner, preferably orally or parenterally, in particular perlingually or intravenously.

In general, it has proved to be advantageous, for intravenous administration, to administer quantities of about 0,001 to 1 mg/kg, preferably of about 0.01 to 0.5 mg/kg, of bodyweight in order to achieve effective results, and the dose for oral administration is about 0.01 to 20 mg/kg, preferably 0.1 to 10 mg/kg, of bodyweight.

In spite of this, it can, where appropriate, be necessary to depart from the said quantities, specifically depending on the bodyweight and on the nature of the route of administration, on the individual reaction to the medicament, on the nature of its formulation, and on the time or interval at which administration is effected. Thus, it can be sufficient in some cases to make do with less than the previously mentioned lowest quantity, whereas, in other cases, the said upper limit must be exceeded. When relatively large quantities are being administered, it can be advisable to divide these into several single doses given throughout the day.

STARTING COMPOUNDS

Example I

Isopropyl 2-amino-4-(3-phenylquinolin-5-yl)-6-oxo-9-hydroxy-1,4,5,9-tetrahydro-cyclopentano [1,2-b]pyridine-3-carboxylate

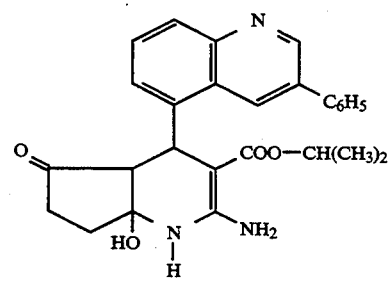

2.94 g (30 mmol) or cyclopentan-1,3-dione, 2.46 g (30 mmol) of sodium acetate and 5.4 g (30 mmol) of isopropyl amidinoacetate hydrochloride are added to 6.99 g (30 mmol) of 3-phenylquinoline-5-carbaldehyde in 90 ml of isopropanol and the mixture is heated at reflux for 7 hours. The product, which has precipitated out, is filtered off with suction and then washed with isopropanol and water and dried. 4.05 g of colourless crystals are obtained with a melting point of 208°–209° C.

PREPARATION EXAMPLES

Example 1

Isopropyl 4-[3-(4-chlorophenyl)-quinolin-5-yl]-2-methyl-5-oxo-1,4-dihydro-cyclo-pentano [1,2-b]pyridine-3-carboxylate

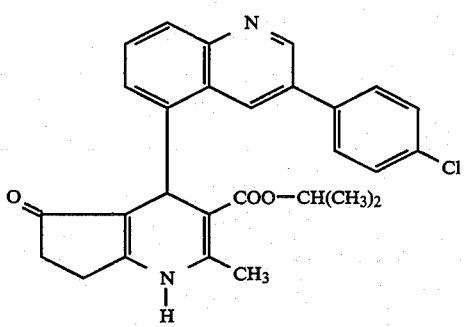

2.67 g (10 mmol) of 3-(4-chlorophenyl)-quinoline-5-carbaldehyde are boiled at reflux for 24 hours in 15 ml of isopropanol and 3.2 ml of acetic acid together with 0.98 g (10 mmol) of cyclopentandione and 1.43 g (10 mmol) of isopropyl 3-aminocrotonate. The mixture is then cooled and concentrated. It is taken up in dichloromethane and washed with water, sodium hydrogen carbonate solution and water once again, and then dried and concentrated. Following recrystallization from ethyl acetate, 1.4 g of colourless crystals are obtained with a melting point of 265°–266° C.

Example 2

Isopropyl 2-amino-4-(3-phenylquinolin-5-yl)-5-oxo-1,4-dihydro -cyclopentano [1,2-b]pyridine-3- carboxylate

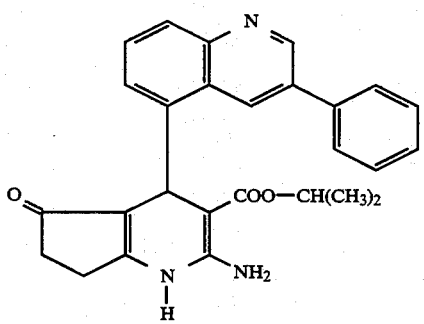

2 ml of trimethylsilylimidazole are added to 2 g of the compound from example I in 30 ml of DMF and the mixture is slowly heated to 90° C. under an atmosphere of argon. After 2 hours, a further 2 ml of trimethylsilylimidazole are added and the mixture is stirred for a further 2 hours. It is then cooled, poured into water and extracted twice with ethyl acetate, and the combined ethyl acetate phases are then washed with water, dried and concentrated. The resulting crude product is purified on a silica gel column using toluene/acetone mixtures. The clean fractions are combined and concentrated. The resulting residue is crystallized with acetonitrile, filtered off with suction and washed with acetonitrile. 560 mg of a colourless substance are obtained with a melting point of 187°–189° C.

The compounds listed in Table 1 are prepared in analogy with the instructions in Examples 1 and 2:

TABLE 1

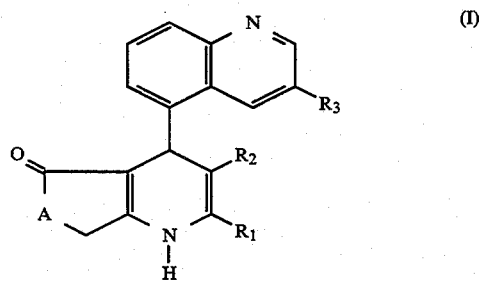

| Ex. No. | $R^1$ | $R^2$ | M.P. °C. |
|---|---|---|---|
| 3 | —NH$_2$ | —CO$_2$C$_2$H$_5$ | 273 |
| 4 | —CH$_3$ | —CO$_2$CH$_3$ | 290 |
| 5 | —CH$_3$ | —CO$_2$C$_2$H$_5$ | 274 |
| 6 | —CH$_3$ | —CO$_2$CH(CH$_3$)$_2$ | 254 |
| 7 | —CH$_3$ | —CO$_2$—(CH$_2$)$_2$—OCH$_3$ | 208–209 |

We claim:
1. A 4-quinolyl-dihydropyridine of the formula (I)

(I)

in which

A represents a sulphur atom or the —CH$_2$-group, $R^1$ represents hydrogen, amino, cyano, formyl or trifluoromethyl, or represents straight-chain or branched alkyl having up to 3 carbon atoms, which is optionally substituted by hydroxyl or by a group of the formula NR$^6$NR$^7$, —O—(CH$_2$)$_a$—OR$^8$ or —O— (CH$_2$)$_b$ —NR$^9$R$^{10}$, in which $R^6$, $R^7$, $R^9$ and $R^{10}$ are identical or different and denote hydrogen, methyl or ethyl, $R^8$ and $R^{8'}$ are identical or different and denote methyl or ethyl, and a and b are identical or different and denote a number 2 or 3, $R^2$ represents a group of the formula —CO—NR$^{11}$R$^{12}$ or —CO—D—R$^{13}$, in which $R^{11}$ and $R^{12}$ are identical or different and denote hydrogen, a straight-chain, branched, cyclic, saturated or unsaturated hydrocarbon radical having up to 6 carbon atoms, which is optionally substituted by fluorine, chlorine, phenyl or pyridyl, or denote phenyl or pyridyl, which are optionally substituted by fluorine, chlorine, methyl or methoxy, or $R^{11}$ and $R^{12}$, together and with the inclusion of the nitrogen atom, form a 5- or 6-membered, unsaturated heterocycle, which is optionally interrupted by oxygen or sulphur or the radical $NR^{15}$, in which $R^{15}$ denotes hydrogen or phenyl, which is optionally substituted by fluorine, chlorine, methyl, methoxy or trifluoromethyl, or denotes a cyclic, saturated or unsaturated, straight-chain or branched hydrocarbon radical having up to 4 carbon atoms, which is optionally substituted by phenyl or pyridyl, D denotes a direct linkage or an oxygen atom, $R^{11}$ denotes hydrogen or phenyl, which is optionally substituted by fluorine, chlorine, methyl, methoxy or trifluoromethyl, or denotes a cyclic, straight-chain or branched saturated or unsaturated hydrocarbon radical having up to 6 carbon atoms, which is optionally interrupted by oxygen or sulphur or by —CO—, —CO—NH—, —NH—CO— or —$NR^{16}$, in which $R^{16}$ has the abovementioned meaning of $R^{15}$ and is identical to or different from the latter, or the hydrocarbon radical is optionally interrupted by phenylidene or by heterocyclic residues of the formulae

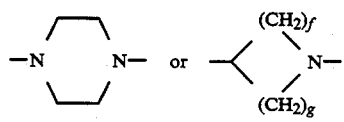

in which, f and g are identical or different and denote a number 1 or 2, and the hydrocarbon radical is optionally substituted by cyclopropyl, cyclobutyl, cyclopentyl, cyclohexyl, fluorine, chlorine, nitro or hydroxyl, or by straight-chain or branched alkylthio or alkoxy having in each case up to 5 carbon atoms, or by phenyl, phenoxy, phenylthio or pyridyl, which are optionally substituted by fluorine, chlorine, methyl, methoxy or methylthio, or can be substituted by a group of the formula —$CONR^{18}R^{19}$ or —$NR^{20}R^{21}$, in which $R^{17}$ has the abovementioned meaning of $R^{15}$ and is identical to or different from the latter and $R^{18}$, $R^{19}$, $R^{20}$ and $R^{21}$ have the abovementioned meaning of $R^{11}$ and $R^{12}$ and are identical to or different from these latter, and $R^3$ represents phenyl, which is optionally substituted by fluorine, chlorine, nitro or trifluoromethyl, or by straight-chain or branched alkyl or alkoxy having in each case up to 4 carbon atoms, or represents thienyl, which is optionally substituted by fluorine or chlorine, or a salt thereof.

2. A compound or salt thereof according to claim 1, in which $R^1$ represents hydrogen, amino or methyl, $R^2$ represents a group of the formula —CO—$NR^{11}R^{12}$ or —CO—D—$R^{13}$, in which $R^{11}$ and $R^{12}$ are identical or different and denote hydrogen or a straight-chain, branched or cyclic alkyl radical having up to 6 carbon atoms, D denotes an oxygen atom, $R^{13}$ denotes hydrogen or straight-chain or branched alkyl having up to 6 carbon atoms, which is optionally substituted by cyclopropyl, cyclobutyl, cyclopentyl or cyclohexyl, or by straight-chain or branched alkoxy or alkylthio having in each case up to 4 carbon atoms, or by fluorine, phenyl, phenoxy or $NR^{20}R^{21}$, in which $R^{20}$ and $R^{21}$ in each case represent hydrogen, or alkyl having up to 4 carbon atoms, which is optionally substituted by phenyl, or phenyl, and $R^3$ represents phenyl, which is optionally substituted fluorine, chlorine, methyl or methoxy, and $R^1$ represents phenyl, which is optionally substituted by fluorine, chlorine, methyl or methoxy, 3. A compound or salt according to claim 1, wherein such compound is isopropyl 2-amino-4-(3-phenylquinolin-5-yl) 5-oxo-1,4-dihydro-cyclopentano [1,2-b] pyridine-3-carboxylate of the formula

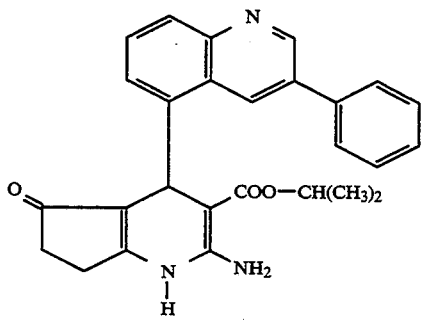

or salt thereof.

4. A compound or salt according to claim 1, wherein such compound is isopropyl 2-amino-4-(3-phenylquinolin-5-yl)-5-oxo-1,4 -dihydro-cyclopentano [1,2-b]pyridine-3-carboxylate of the formula

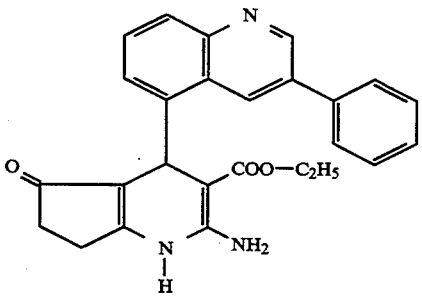

or salt thereof

5. A compound or salt according to claim 1, wherein such compound is methyl 2-methyl-4-(3-phenylquinolin-5-yl) 5-oxo-1,4-dihydro-cyclopentano [1,2-b]pyridine-3-carboxylate of the formula

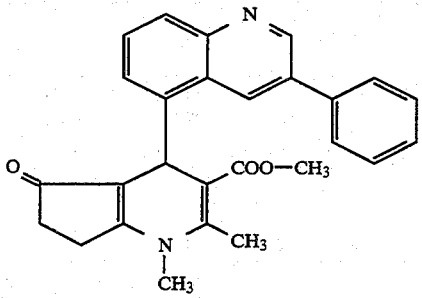

or salt thereof.

6. A compound or salt according to claim 1, wherein such compound is isopropyl 2-methyl-4-(3-phenyl-quinolin-5-yl)-5-oxo-1, 4-dihydro-cyclopentano [1,2-b] pyridine-3-carboxylate of the formula

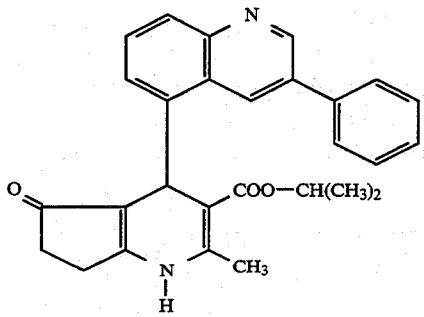

7. A composition suitable for increasing the contractile power of the heart comprising an amount effective therefor of a compound or salt thereof according to claim 1 and a diluent.

8. A method of increasing the contractile power of the heart of a patient in need thereof which comprises administering to such patient in need thereof an amount effective therefor of a compound or salt thereof according to claim 1.

9. A method of improving the tone of the smooth musculature of a patient in need thereof which comprises, administering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,436,342
DATED : July 25, 1995
INVENTOR(S) : Goldman, et al.

It is certified that error appears in the above-indentified patent and that said Letters Patent is hereby corrected as shown below:

Title Page — ABSTRACT: Line 2 delete " dhydropyridines " and substitute -- dihydropyridines --

Col. 16, line 51 — Delete " $NRNR^6R^7$ " and substitute -- $NR^6R^7$ --

Col. 17, line 17 — Delete " $R^{11}$ " and substitute -- $R^{13}$ --

Signed and Sealed this

Ninth Day of April, 1996

Attest:

BRUCE LEHMAN

Attesting Officer

Commissioner of Patents and Trademarks